United States Patent
Duke

(10) Patent No.: US 12,217,843 B2
(45) Date of Patent: *Feb. 4, 2025

(54) BOLUS CALCULATOR WITH PROBABILISTIC CARBOHYDRATE MEASUREMENTS

(71) Applicant: Roche Diabetes Care, Inc., Indianapolis, IN (US)

(72) Inventor: David L. Duke, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1345 days.

This patent is subject to a terminal disclaimer.

(21) Appl. No.: 16/386,696

(22) Filed: Apr. 17, 2019

(65) Prior Publication Data

US 2019/0244715 A1    Aug. 8, 2019

Related U.S. Application Data

(63) Continuation of application No. 15/140,550, filed on Apr. 28, 2016, now Pat. No. 10,311,976.

(51) Int. Cl.
*G16H 20/10* (2018.01)
*G16H 20/60* (2018.01)
*G16H 50/30* (2018.01)

(52) U.S. Cl.
CPC ............ *G16H 20/10* (2018.01); *G16H 20/60* (2018.01); *G16H 50/30* (2018.01)

(58) Field of Classification Search
CPC ......... G16H 50/20–50/30; G16H 20/10–2017; A61B 5/4836–5/4839; A61B 5/7275
See application file for complete search history.

(56) References Cited

U.S. PATENT DOCUMENTS

| | | |
|---|---|---|
| 6,572,545 B2 | 6/2003 | Knobbe et al. |
| 6,575,905 B2 | 6/2003 | Knobbe et al. |
| 7,291,107 B2 | 11/2007 | Hellwig et al. |

(Continued)

FOREIGN PATENT DOCUMENTS

| | | |
|---|---|---|
| EP | 2762073 A1 | 8/2014 |
| WO | 2002/24065 A1 | 3/2002 |

(Continued)

OTHER PUBLICATIONS

Klonof, David C. "The current status of bolus calculator decision-support software." Journal of diabetes science and technology 6.5 (2012): 990-994 (Year: 2012).*

(Continued)

*Primary Examiner* — Karlheinz R. Skowronek
*Assistant Examiner* — Joseph Pulliam
(74) *Attorney, Agent, or Firm* — Dinsmore & Shohl LLP

(57) ABSTRACT

Methods and devices involving using a bolus calculator to account for an uncertainty of a carbohydrate estimate to reduce a risk of hypoglycemia and/or a risk of hyperglycemia. More specifically, methods and devices using an algorithm executed by a processor of the bolus calculator and using a carbohydrate estimate and a measure defining the uncertainty of the carbohydrate estimate to determine the probability of hypoglycemia and/or hyperglycemia if the carbohydrate estimate is an overestimate or an underestimate, and subsequently providing recommendations and alerts to a user.

20 Claims, 5 Drawing Sheets

(56) References Cited

U.S. PATENT DOCUMENTS

| | | | |
|---|---|---|---|
| 7,395,158 | B2 | 7/2008 | Monfre et al. |
| 7,785,313 | B2 | 8/2010 | Mastrototaro |
| 8,579,854 | B2 | 11/2013 | Budiman et al. |
| 8,579,879 | B2 | 11/2013 | Palerm et al. |
| 8,684,922 | B2 | 4/2014 | Tran |
| 8,734,422 | B2 | 5/2014 | Hayter |
| 8,843,321 | B2 | 9/2014 | Duke et al. |
| 8,977,504 | B2 | 3/2015 | Hovorka |
| 10,299,737 | B2 * | 5/2019 | Essenpreis |
| 2002/0106709 | A1 | 8/2002 | Potts et al. |
| 2004/0167464 | A1 | 8/2004 | Ireland et al. |
| 2006/0047192 | A1 | 3/2006 | Hellwig et al. |
| 2008/0154513 | A1 * | 6/2008 | Kovatchev ............. G16H 15/00 702/19 |
| 2009/0105572 | A1 | 4/2009 | Malecha |
| 2010/0145670 | A1 * | 6/2010 | Alferness ................ G16Z 99/00 703/11 |
| 2010/0262434 | A1 | 10/2010 | Shaya |
| 2011/0054439 | A1 * | 3/2011 | Yodfat .................. G16H 40/67 604/503 |
| 2011/0071464 | A1 | 3/2011 | Palerm |
| 2011/0184267 | A1 | 7/2011 | Duke et al. |
| 2011/0257627 | A1 | 10/2011 | Hovorka |
| 2011/0313674 | A1 | 12/2011 | Duke et al. |
| 2012/0165638 | A1 | 6/2012 | Duke et al. |
| 2012/0166126 | A1 | 6/2012 | Engelhardt et al. |
| 2014/0005505 | A1 | 1/2014 | Peyser et al. |
| 2014/0066884 | A1 | 3/2014 | Keenan et al. |
| 2014/0066887 | A1 | 3/2014 | Mastrototaro et al. |
| 2014/0081103 | A1 | 3/2014 | Schaible |
| 2014/0083867 | A1 | 3/2014 | Schaible |
| 2014/0088392 | A1 | 3/2014 | Bernstein et al. |
| 2014/0100435 | A1 | 4/2014 | Duke et al. |
| 2014/0118138 | A1 | 5/2014 | Cobelli et al. |
| 2014/0187887 | A1 | 7/2014 | Dunn et al. |
| 2014/0188400 | A1 | 7/2014 | Dunn et al. |
| 2014/0221966 | A1 | 8/2014 | Buckingham et al. |
| 2014/0235981 | A1 | 8/2014 | Hayter |
| 2015/0273147 | A1 | 10/2015 | Duke et al. |

FOREIGN PATENT DOCUMENTS

| | | | |
|---|---|---|---|
| WO | 2013/032965 | A1 | 3/2013 |
| WO | 2014/106263 | A2 | 7/2014 |
| WO | 2015/183689 | A1 | 3/2015 |
| WO | 2015073211 | A1 | 5/2015 |

OTHER PUBLICATIONS

Roadbard, D. "Hypo- and Hyperglycemia in Relation to the Mean, Standard Deviation, Coefficient of Variation, and Nature of the Glucose Distribution"; Diabetes Technology & Therapeutics, vol. 14, No. 10, 2012; p. 868-876. (Year: 2012).*
Xie, Q. et al; "Meal Detection and meal size estimation for Type 1 Diabetes Treatment: A variable State Dimension Approach"; Proceedings of the ASME 2015 Dynamic Systems and Control Conference, DSCC2015; Oct. 28-30, 2015, Columbus, Ohio, USA; p. 1-10. (Year: 2015).*
Lucero et al., "On the Registration of Time and the Patterning of Speech Movements," Journal of Speech, Language, and Hearing Research 40: 1111-1117.
Kaufman et al., Finding Groups in Data: An Introduction to Cluster Analysis (1 ed.), New York: John Wiley, ISBN J-471-87876-6 (Book).
Sakoe et al., "Dynamic Programming Algorithm Optimization for Spoken Word Recognition," IEEE Transactions on Acoustics, Speech and Signal Processing 26 (1 ): 43-49, p. 43-49.
Takita et al., "Cluster Analysis of Self-Monitoring Blood Glucose Assessments in Clinical Islet Cell Transplantation for Type 1 Diabetes," Diabetes Care, vol. 34, 2011, 1799-1803.
Bruno Sinopoli, et al., Kalman Filtering With Intermittent Observations, DARPA under grant F33615-01-C-1895, J8 pages, 2009.

David Di Ruscio, Closed and Open Loop Subspace System Identification of the Kalman Filler, 2009 Norwegian Society of Automatic Control, vol. 30, No. 2, 2009, pp. 71-86, ISSN 1890-1328, Norway.
J. Zico Kolter, et al., A Probabilistic Approach to Mixed Open-loop and Closed-loop Control, with Application to Extreme Autonomous Driving, Computer Science Department, Stanford University, California (kolter@cs.stanford.edu) 7 pages, USA, 2010.
Chiara Toffanin, et al., Artificial Pancreas: Model Predictive Control Design from Clinical Experience, Journal of Diabetes Science and Technology, pp. 1470-1483, vol. 7, Issue 6, Nov. 2013, USA.
Signe Schmidt, et al., Model-Based Closed-Loop Glucose Control in Type 1 Diabetes: The DiaCon Experience, Journal of Diabetes Science and Technology, pp. 1255-1264, vol. 7, Issue 5, Sep. 2013, USA.
Schwartz et al., "Use of Automated Bolus Calculators for Diabetes Management," Diabetes Management, Touch Medical Media 2013, 92-95.
International Search Report and Written Opinion completed Jun. 10, 2016 pertaining to PCT/US2016/025502 filed Apr. 1, 2016.
Kovatchev et al., "Symmetrization of the Blood Glucose Measurement Scale and Its Applications,", Diabetes Care, 1997, vol. 20, No. 11, 1655-1658.
Lucero et al., "On the Registration of Time and the Patterning of Speech Movements," Journal of Speech, Language, and Hearing Research 40: 1111-1117, 1997.
Ward, "Hierarchical Grouping to Optimize an Objective Function," Journal of the American Statistical Association, 1963, vol. 58, Issue 301, 236-244.
Kaufman et al., Finding Groups in Data: An Introduction to Cluster Analysis (1 ed.), New York: John Wiley, ISBN J-471-87876-6 (Book), 2005.
Sakoe et al., "Dynamic Programming Algorithm Optimization for Spoken Word Recognition," IEEE Transactions on Acoustics, Speech and Signal Processing 26 (1 ): 43-49, 1978.
Takita et al., "Cluster Analysis of Self-Monitoring Blood Glucose Assessments in Clinical Islet Cell Transplantation for Type 1 Diabetes," Diabetes Care, vol. 34, 2011, 1799-1803, 2011.
International Search Report pertaining to Appln. No. PCT/US2017/019030, filed Feb. 23, 2017, 5 pages.
Written Opinion pertaining to Appln. No. PCT/US2017/019030, filed Feb. 23, 2017, 9 pages.
International Search Report pertaining to Appln. No. PCT/US2017/019025, filed Feb. 23, 2017, 5 pages.
Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.
U.S. Non-Final Office Action dated Sep. 5, 2017 pertaining to U.S. Appl. No. 14/677,148, 13 Pages.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.

(56) References Cited

OTHER PUBLICATIONS

Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
U.S. Non-Final Office Action dated May 31, 2018 pertaining to U.S. Appl. No. 15/170,468, 12 pages.
Pickup et al. (Continuous Subcutaneous Insulin Infusion at 25 Years, Diabetes Care 2002, 25, 593-598).

* cited by examiner

13

How sure are you of the carbohydrate estimate?

A. Certain – I looked it up
On my phone or my phone
provided an estimate based on
a captured image B. Pretty Sure – Making a reasonable estimate based on similar meals C. Unsure – guessing

BOLUS CALCULATOR WITH PROBABILISTIC CARBOHYDRATE MEASUREMENTS

CROSS-REFERENCE TO RELATED APPLICATIONS

This application is the continuation of U.S. patent application Ser. No. 15/140,550, entitled "BOLUS CALCULATOR WITH PROBABILISTIC CARBOHYDRATE MEASUREMENTS," filed on Apr. 28, 2016, the entirety of which is incorporated by reference herein.

TECHNICAL FIELD

This application relates generally to methods and devices involving using a bolus calculator to account for an uncertainty of a carbohydrate estimate to reduce a risk of hypoglycemia and a risk of hyperglycemia. More specifically it relates to methods and devices using an algorithm executed by a processor of the bolus calculator and using a carbohydrate estimate and a measure defining the uncertainty of the carbohydrate estimate to determine the risk (or probability) of hypoglycemia and hyperglycemia if the carbohydrate estimate is an overestimate or an underestimate, respectively, and subsequently providing recommendations and alerts to a user.

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare may involve both establishing a therapeutic program and monitoring the progress of the afflicted person. Monitoring blood glucose levels is an important process that is used to help diabetics maintain blood glucose levels as near as normal as possible throughout the day. Monitoring can also allow successful treatment of a diabetic by altering therapy as necessary. Monitoring may allow the diabetic to monitor more closely his or her condition and, in addition, can provide information of value to the healthcare provider in determining both progress of the patient and detecting any need to change the patient's therapy program.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a noncontinuous system may require a diabetic to apply a blood sample to reagent-impregnated region of a test strip, wipe the blood sample from the test strip after a predetermined period of time, and determine blood glucose level by comparing the color of the reagent-impregnated regions of the test strip with a color chart supplied by the test strip manufacturer. Alternatively, many patients use continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every minute, and transmit the results of the glucose measurement result to an electronic monitor.

Embodiments described herein provide safer, more efficient methods for individuals requiring multiple daily injections who have difficulty counting carbohydrates; the embodiments also are beneficial for patients using CGM who want help handling meals. Embodiments detail calculations using an algorithm that improve the accuracy of the bolus calculator by accounting for uncertainty.

BRIEF SUMMARY

Embodiments described herein provide for a method of using bolus calculator to account for an uncertainty of a carbohydrate estimate to reduce a risk of hypoglycemia and/or a risk of hyperglycemia comprising: providing the bolus calculator containing therewithin a processor that when activated executes an algorithm defining pre-set values for: a first threshold percentage defining a probability of hypoglycemia ($P_{hypo}$); and/or a second threshold percentage defining a probability of hyperglycemia ($P_{hyper}$); and/or a hypoglycemia threshold ($T_{hypo}$); and/or a hyperglycemia threshold ($T_{hyper}$); and providing to the bolus calculator the carbohydrate estimate and a measure defining the uncertainty of the carbohydrate estimate (c); activating the processor to execute the algorithm to use the pre-set values, the carbohydrate estimate and the measure defining the uncertainty of the carbohydrate estimate to: determine the risk (or probability) of hypoglycemia if the carbohydrate estimate has overestimated the carbohydrate content and therefore a standard meal insulin bolus has been overestimated and thus should be adjusted to reduce the risk of hypoglycemia; and/or determine the risk (or probability) of hyperglycemia if the carbohydrate estimate has underestimated the carbohydrate content and therefore the standard meal insulin bolus has been underestimated and thus should be adjusted to reduce the risk of hyperglycemia; and/or providing a recommendation to the user when the carbohydrate estimate has been overestimated to adjust a corresponding meal insulin bolus, and alerting the user when the carbohydrate estimate has been underestimated recommending a postprandial glucose measurement.

Additional embodiments described herein provide for a method of using a bolus calculator to account for an uncertainty of a carbohydrate estimate to reduce a risk of hypoglycemia and/or a risk of hyperglycemia comprising: providing the bolus calculator containing therewithin a processor that when activated executes an algorithm defining pre-set values for: a first threshold percentage defining a probability of hypoglycemia ($P_{hypo}$); and/or a second threshold percentage defining a probability of hyperglycemia ($P_{hyper}$); and/or a hypoglycemia threshold ($T_{hypo}$); and/or a hyperglycemia threshold ($T_{hyper}$); and providing to the bolus calculator the carbohydrate estimate (c) and a standard deviation ($\sigma_c$) defining the uncertainty of the carbohydrate estimate; activating the processor to execute the algorithm; determining the risk (probability) of hypoglycemia if the carbohydrate estimate has overestimated the carbohydrate content and therefore a standard meal insulin bolus has been overestimated and thus should be adjusted to reduce the risk of hypoglycemia by: calculating the standard meal insulin bolus ($I_{meal}$) utilizing the carbohydrate estimate and a carbohydrate ratio of a user; calculating, using the carbohydrate estimate, the standard deviation, and a parameter on a normal cumulative distribution, a first level ($C_{Phypo}$) corresponding to the threshold percentage defining the probability of hypoglycemia; calculating a hypoglycemia-averse insulin bolus ($I_{hypo(x)\%}$) using an insulin sensitivity factor of the user, the hypoglycemia threshold and the calculated first level; comparing the standard meal insulin bolus with the hypoglycemia-averse insulin bolus; selecting the minimum of the standard meal insulin bolus and the hypoglycemia-averse insulin bolus thereby accounting for the risk of hypoglycemia; and/or determining the risk (probability) of hyperglycemia if the carbohydrate estimate has underestimated the carbohydrate content and therefore the standard meal insulin bolus has been underestimated and thus should be adjusted to reduce the risk of hyperglycemia by: calculating, using the carbohydrate estimate, the standard deviation, and a parameter on a normal cumulative distribution, a second level (CPhyper) corresponding to the threshold percentage defining the probability of hyperglycemia; calculating, using the calculated second level, the user insulin sensitivity factor, and the target glucose level, a value representing a post-prandial glucose estimate; comparing the value to the hyperglycemia threshold; and providing an alert to the user instructing the user to take a post-prandial glucose measurement when the value is greater than the hyperglycemia threshold, thereby accounting for the risk of hyperglycemia.

Yet additional embodiments herein provide for a method for a bolus calculator to account for an uncertainty of a carbohydrate estimate to reduce a risk of hypoglycemia and/or a risk of hyperglycemia comprising: a processor that when activated is configured to execute an algorithm defining pre-set values for: a first threshold percentage defining a probability of hypoglycemia ($P_{hypo}$); and/or a second threshold percentage defining a probability of hyperglycemia ($P_{hyper}$); and/or a hypoglycemia threshold ($T_{hypo}$); and/or a hyperglycemia threshold ($T_{hyper}$); and the processor is configured, upon the bolus calculator receiving the carbohydrate estimate and a standard deviation ($\sigma_c$) defining the uncertainty of the carbohydrate estimate (c), to: determine the risk (probability) of hypoglycemia if the carbohydrate estimate has overestimated the carbohydrate content and therefore a standard meal insulin bolus has been overestimated and thus should be adjusted to reduce the risk of hypoglycemia by: calculating the standard meal insulin bolus ($I_{meat}$) utilizing the carbohydrate estimate and a carbohydrate ratio of a user; calculating, using the carbohydrate estimate, the standard deviation, and a parameter on a normal cumulative distribution, a first level ($C_{Phypo}$) corresponding to the threshold percentage defining the probability of hypoglycemia; calculating a hypoglycemia-averse insulin bolus ($I_{hypo(x)\%}$) using an insulin sensitivity factor of the user, the hypoglycemia threshold and the calculated first level; comparing the standard meal insulin bolus with the hypoglycemia-averse insulin bolus; selecting the minimum of the standard meal insulin bolus and the hypoglycemia-averse insulin bolus thereby accounting for the risk of hypoglycemia; and/or determine the risk (probability) of hyperglycemia if the carbohydrate estimate has underestimated the carbohydrate content and therefore the standard meal insulin bolus has been underestimated and thus should be adjusted to reduce the risk of hyperglycemia by: calculating, using the carbohydrate estimate, the standard deviation, and a parameter on a normal cumulative distribution, a second level ($C_{Phyper}$) corresponding to a percentage defining the probability of hyperglycemia; calculating, using the calculated second level, the user insulin sensitivity factor, and the target glucose level, a value representing a post-prandial glucose estimate; comparing the value to the hyperglycemia threshold; and providing an alert to the user instructing the user to take a post-prandial glucose measurement when the value is greater than the hyperglycemia threshold, thereby accounting for the risk of hyperglycemia.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about," which is intended to mean up to ±10% of an indicated value. Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of embodiments of the invention are approximations, the numerical values set forth in the specific examples are reported as precisely as possible. Any numerical values, however, inherently contain certain errors necessarily resulting from error found in their respective measurements.

Parts of methods described herein such as mathematical determinations, calculations, inputting of data for computations or determinations of equations or parts thereof can be performed on parts of or one or more computers or computer systems that can include one or more processors, as well as software to run or execute programs and run calculations or computations.

Methods and systems and parts thereof described herein can be combined so as to implement embodiments of the invention. Forms of words used herein can have variations: for example when a word such as "form" is used, this implies that variations such as "calculate" and "calculating" are understood and have been considered.

As user herein, "user," "patient," and "person" are used to refer to an individual interacting with the CGM system to improve that individual's health via improvements described herein.

Figure 1:
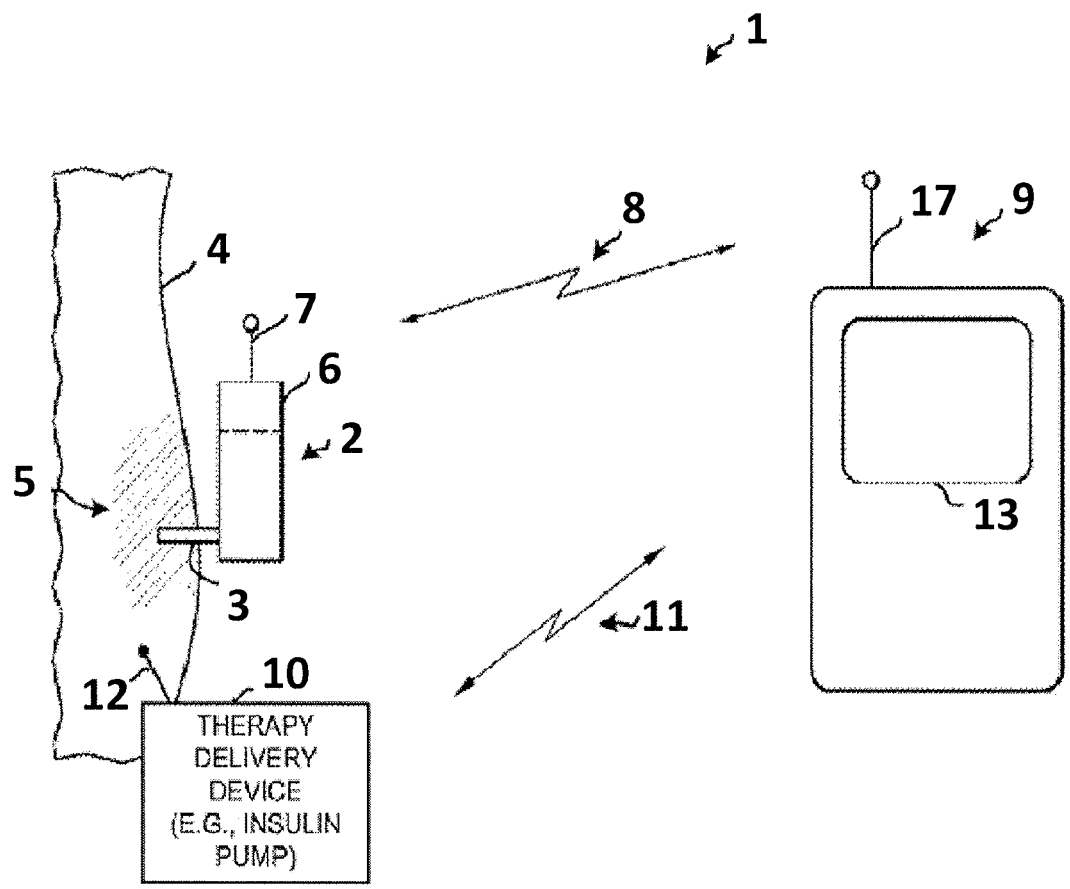
FIG. 1 illustrates a continuous glucose monitoring (CGM) system according to one or more embodiments described herein.

Referring to FIG. 1, an exemplary CGM system 1 is illustrated for monitoring the glucose level of a person having diabetes. In particular, the CGM system 1 is operative to collect a measured glucose value at a predetermined, adjustable interval, such as every one minute, five minutes, or at other suitable intervals. The CGM system 1 illustratively includes a glucose sensor 2 having a needle or probe 3 that is inserted under a skin 4 of the person. The end of the needle 3 is positioned in a region containing an interstitial fluid 5 such that measurements taken by the glucose sensor 2 are based on the level of glucose in the interstitial fluid 5. The needle can also be placed in a region with blood and/or other bodily fluid. The glucose sensor 2 is positioned adjacent the abdomen of the person or at another suitable location. The glucose sensor 2 may comprise other components as well, including but not limited to a wireless transmitter 6 and an antenna 7. The glucose sensor 2 may alternatively use other suitable devices for taking measurements, such as, for example, a non-invasive device (e.g., an infrared light sensor). Upon taking a measurement, the glucose sensor 2 transmits the measured glucose value(s) via a communication link 8 to a computing device 9, illustratively a blood glucose management device 9 or a bolus calculator 9 (in specific embodiments the bolus calculator has a housing, as described herein, and is a stand-alone device, working in conjunction with the processor(s) 14 which includes the bolus calculator module 19 performing logic properties of, for example, the bolus calculator 9).

The CGM system 1 further includes a therapy delivery device 10, illustratively an insulin infusion pump 10, for delivering therapy (e.g., insulin) to the person. The pump 10 can have a single housing or can have a two-part housing where one part is reusable and the other disposable, where the disposable part can include a power source such as a battery. The insulin pump 10 is in communication with the management device 9 via a communication link 11, and the management device 9 is able to communicate bolus and basal rate information to the insulin pump 10. The insulin pump 10 includes a catheter 12 having a needle that is inserted through the skin 4 of the person for injecting the insulin. Insulin pump 10 is illustratively positioned adjacent the abdomen of the person or at another suitable location. Similar to the glucose sensor 2, the infusion pump 10 also includes a wireless transmitter and an antenna for communication with management device 9. The insulin pump 10 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 9. Similarly, the basal rate of the basal insulin is set based on user input or in response to a command from management device 9. Infusion pump 10 may include a display 13 for displaying pump data and a user interface providing user controls. In an alternative embodiment, insulin pump 10 and the glucose sensor 2 may be provided as a single device worn by the patient, and at least a portion of the logic provided by a processor 14 (FIG. 2) may reside on this single device. Bolus insulin may also be injected by other means, such as manually by the user via a needle.

Communication links 8, 11 are illustratively wireless, such as a radio frequency ("RF") or other suitable wireless frequency, in which data and controls are transmitted via electromagnetic waves between the sensor 2, the therapy delivery device 10, and the management device 9. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 8, 11 may facilitate communication between multiple devices, such as between the glucose sensor 2, the computing device 9, the insulin pump 10, and other suitable devices or systems. Wired links may alternatively be provided between devices of the system 1, such as, for example, a wired Ethernet link. Other suitable public or proprietary wired or wireless links may be used.

Figure 2:
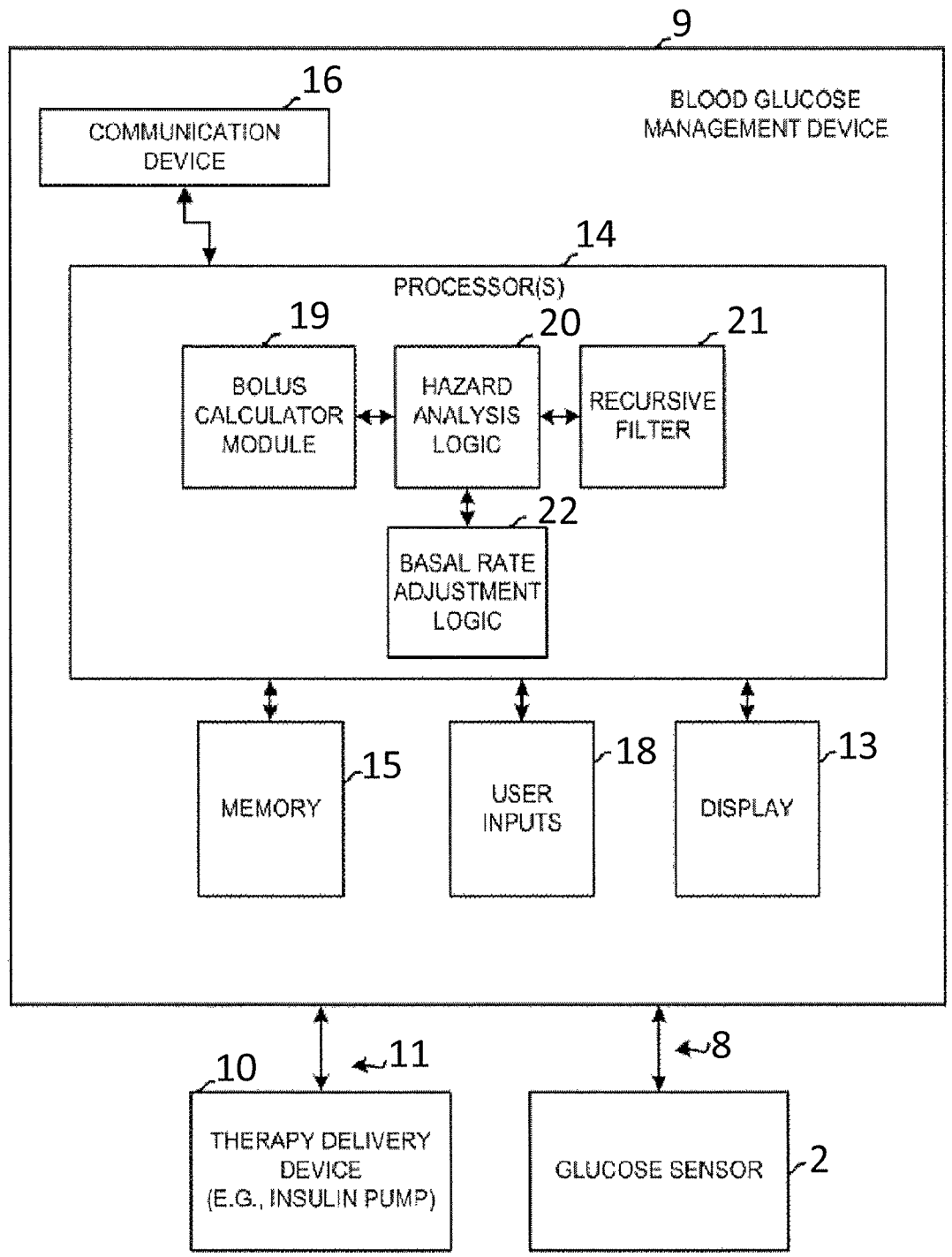
FIG. 2 illustrates an exemplary blood glucose management device, therapy delivery device, and glucose sensor of the CGM system of FIG. 1, the blood glucose management device including a bolus calculator module, hazard analysis logic, and basal rate adjustment logic.

FIG. 2 illustrates an exemplary embodiment of the management device 9 of the CGM system 1 of FIG. 1. The management device 9 includes at least one processing device 14 that executes software and/or firmware code stored in a memory 15 of management device 9. The software/firmware code contains instructions that, when executed by the processor 14 of the management device 9, causes the management device 9 to perform the functions described herein. The management device 9 may alternatively include one or more application-specific integrated circuits (ASICs), field-programmable gate arrays (FPGAs), digital signal processors (DSPs), hardwired logic, or combinations thereof. While the management device 9 is illustratively a glucose monitor 9, other suitable management devices 9 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although the management device 9 is illustrated as a single management device 9, multiple computing devices may be used together to perform the functions of the management device 9 described herein. FIG. 2 can also include the bolus calculator module 19, a hazard analysis logic component 20 (such as for accounting for time/rates of change of glucose levels in calculations), a recursive filter 21 (such as for removing noise in calculations or adjusting for the probability of glucose sensor accuracy), and/or a basal rate adjustment logic component 22 (such as for adjusting for the effect of the user activities on rates in calculations).

The memory 15 is any suitable computer readable medium that is accessible by the processor 14. The memory 15 may be a single storage device or multiple storage devices, may be located internally or externally to the management device 9, and may include both volatile and non-volatile media. Further, the memory 15 may include one or both of removable and non-removable media. Exemplary memory 15 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the management device 9.

The management device 9 further includes a communication device 16 operatively coupled to processor 14. The communication device 16 includes any suitable wireless and/or wired communication module operative to transmit and receive data and controls over the communication links 8, 11 between the device 9 and the glucose sensor 2 and the insulin pump 10. In one embodiment, the communication device 16 includes an antenna 17 (FIG. 1) for receiving and/or transmitting data wirelessly over the communication links 8, 11. The management device 9 stores in the memory 15 measured glucose results and other data received from the glucose sensor 2 and/or the insulin pump 10 via the communication device 16.

The management device 9 includes one or more user input devices 18 for receiving user input. The input devices 18 may include pushbuttons, switches, a mouse pointer, keyboard, touch screen, or any other suitable input device. The display 13 is operatively coupled to the processor 14. The display 13 may comprise any suitable display or monitor technology (e.g., liquid crystal display, etc.) configured to display information provided by the processor 14 to the user. Processor 14 is configured to transmit to the display 13 information related to the detected glucose state of the person, the risk associated with the glucose state, and basal rate and bolus information. The glucose state may include the estimated glucose level and/or the estimated rate-of-change of the glucose level, as well as an estimate of the quality or uncertainty of the estimated glucose level. Moreover, the displayed information may include warnings and/or alarms, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as from about 50 to about 70 mg/dL of glucose in blood. Management device 9 may also be configured to communicate information or warnings to the person via a sense of touch, such as for example by vibrating.

In one embodiment, the management device 9 is in communication with a remote computing device, such as at a caregiver's facility or a location accessible by a caregiver, and data (e.g., glucose data or other physiological information) is transferred between them. In this embodiment, management device 9 and the remote device are configured to transfer physiological information through a data connection such as, for example, via the Internet, cellular communications, or the physical transfer of a memory device such as a diskette, USB key, compact disc, or other portable memory device.

Specific embodiments of methods and devices as described herein may include setting the threshold percentage defining the probability of hypoglycemia at about five percent, and setting the threshold percentage defining the probability of hyperglycemia at about seventy-five percent. Other embodiments involve setting the threshold percentage defining the probability of hypoglycemia at between about ten percent and twenty-five percent, and/or setting the threshold percentage defining the probability of hyperglycemia between about seventy percent to about eighty percent.

Specific embodiments include coupling the bolus calculator with a physically separate memory or a memory within the bolus calculator such that the standard deviation is derived in part from the medical history of the user. In yet other embodiments including the memory, the standard deviation is derived in part from previous determinations of the user as to an ability to estimate carbohydrates. In other specific embodiments comprising the memory, the standard deviation is derived in part from previous tests provided to the user testing estimating carbohydrates.

Specific embodiments comprise the user providing to the bolus calculator the carbohydrate estimate. The bolus calculator can query the user as to the certainty of the carbohydrate estimate provided by the user, and providing the user with options detailing the uncertainty that can be selected.

Specific embodiments comprise providing, visually via the display, the alert to the user instructing the user to take the post-prandial glucose measurement.

Methods and devices described herein can be used instead of or with a system in conjunction with methods described in commonly owned U.S. patent application Ser. No. 14/677,148, the disclosure of which is hereby incorporated by reference in its entirety.

Specific embodiments herein comprise an alert. More specifically, the alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert.

Specific embodiments herein comprise an alert. More specifically, the alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert.

In one example, an event or a pattern can trigger an alert that can be used to alert the patient to take specific actions whenever a particular event occurs. For example, the pattern can be a post-prandial event, hypoglycemic event, exercise, meals, etc. or any other problematic event or pattern that has occurred in the patient's past physiological data. Thus, when the event is detected again on a real-time basis, the system 1 will alert the patient to that fact such as via the display 13 and/or vibration and/or noise. The bolus calculator can have the processor 14 or multiple processors 14 (including the bolus calculator module 19) interacting with various hardware and/or software to send the alert to a clinician if the person's glucose level falls below (or is predicted to fall below) a predetermined hypoglycemic threshold; an alert can also be sent if the measure of uncertainty is above a certain point. The bolus calculator can be configured to transmit the alert wirelessly and activate an application on the clinician's computer when the computer comes online and/or is otherwise turned on/activated.

EXAMPLES

Utilization of the Algorithm

A carbohydrate estimate is provided along with a measure of its uncertainty. This can include a standard deviation and/or variance. The method uses the bolus calculator in the form of an algorithm that is processed the processor 14 or multiple processors 14 (including the bolus calculator module 19). The uncertainty may be provided by an assessment of a user's ability to count carbohydrates either from a test, or from the user's history. The uncertainty can also be provided by asking the user how sure the user is of the carbohydrate estimate. In some cases the user may be, for example, at a new restaurant, so they can be given, by the bolus calculator, a set of three options for how certain they are regarding the carbohydrate estimate.

Methods and devices herein can use one or two threshold percentage values that can be defined as the probability of post-prandial hypoglycemia ($P_{hypo}$) and the probability of post-prandial hyperglycemia ($P_{hyper}$), respectively. In one specific embodiment the thresholds can be set as follows:

$$P_{hypo} = 5\%$$

$$P_{hyper} = 75\%$$

The algorithm can take action when the probably of post-prandial hypoglycemia exceeds the threshold and/or when the probability of post-prandial hyperglycemia exceeds its threshold. It is possible for both thresholds to be crossed if the uncertainty is high.

The hypoglycemia threshold ($T_{hypo}$) and the hyperglycemia threshold ($T_{hyper}$) can be set and/or pre-set. In one specific embodiment the thresholds can be set as follows:

$$T_{hypo} = 70 \frac{mg}{dl}$$

$$T_{hyper} = 250 \frac{mg}{dl}$$

In specific examples the algorithm is provided a carbohydrate estimate (c) and a standard deviation (c, $\sigma_c$) that defines the uncertainty. The algorithm can also calculate using the carbohydrate ratio (CR), and insulin sensitivity, IS of the user.

In specific examples a step is performed to identify if the standard meal bolus should be adjusted to reduce risk of hypoglycemia. This occurs if the actual carbohydrate content is overestimated. The parameter equivalent to the 5% line can be used in the calculation below:

$$c_{5\%} = c - 1.6449 \cdot \sigma_c$$

In other specific embodiments, the value for ($g_{x\%}$) can be defined such that the x represents up to about twenty-five percent or up to thirty percent. In yet other embodiments the x value can be about five, about ten percent, about fifteen percent, about twenty percent, twenty-five percent, thirty percent. In yet other embodiments the x value can be selected form a range from about five percent to about ten percent or from about one percent to about ten percent, or from about one percent to about twenty percent (Also, the threshold percentage defining a probability of hypoglycemia ($P_{hypo}$) and the threshold percentage defining a probability of hyperglycemia ($P_{hyper}$) can be set at such levels). Also, the parameter −1.6449 can be used; however other parameters that can be used for ($I_{hypo(x)\%}$)($g_{x\%}$) calculations, with associated percentages (that can be used for x) are: −1.28155 for ten percent, −1.751 for four percent, −1.96 for two-point five percent, −2.326 for one percent, and/or −2.576 for one-half percent. The bolus calculator can automatically select, via the processor, between the percentages. Also using the percentages to set a preset threshold percentage defining a probability of hypoglycemia ($P_{hypo}$). Another methods of calculating would be to use a relative error bounds.

The standard meal insulin dose and the hypoglycemia-averse meal insulin dose are calculated. The standard dose divides the carbohydrate estimate by the carbohydrate ratio as shown below:

$$I_{meal} = \frac{c}{CR}$$

The hypoglycemia-averse method assumes an overestimated carbohydrate value and is calculated as shown below:

$$I_{hypo5\%} = \frac{g_t - T_{hypo}}{IS} + \frac{c_{5\%}}{CR}$$

If the value for $I_{hypo5\%}$ is less than $I_{meal}$ then $I_{hypo5\%}$ can be selected. Selecting the minimum of the standard meal insulin bolus and the hypoglycemia-averse insulin bolus can be used to account for the risk of hypoglycemia; the minimum value can be used to adjust a meal bolus or can be used as the meal bolus. The calculation for obtaining the minimum value is shown below:

$$I = \min(I_{meal}, I_{hypo5\%})$$

After the risk of hypoglycemia has been accounted for, the risk of hyperglycemia is evaluated. If the risk of hyperglycemia is greater than $T_{hyper}$ then a reminder for a post-prandial measurement can be set. Post-prandial hyperglycemia occurs when the carbohydrate estimate is too low. First, the carbohydrate estimate associated with $P_{hyper}$ is determined, as shown below:

$$c_{75\%} = c + 0.6745 \cdot \sigma_c$$

The potential insulin dose error is then multiplied by the insulin sensitivity factor and added to the target to get an estimate of the post-prandial glucose value. This is compared to the hyperglycemia threshold as shown below. If the left side of the equation has a greater value than the right ($T_{hyper}$), then there is a 25% probability of post-prandial hyperglycemia. This threshold can be adjusted to reduce alarms.

$$\left(\frac{c_{75\%}}{CR} - I\right) \cdot IS + g_t > T_{hyper}$$

Results

Figures 3A, 3B:
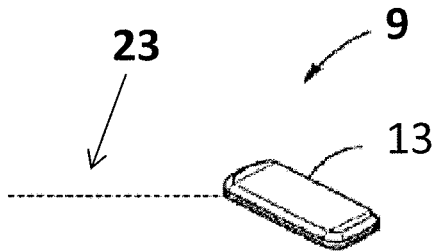
FIG. 3A illustrates an example embodiment of a computing device wherein the computing device is a smart phone having a camera for image capture.
FIG. 3B illustrates the display of the smart phone of the computing device illustrating a query from the smart phone to determine from a user a measure of the certainty of a carbohydrate estimate.

The algorithm described above can be used in various ways for specific results. In specific embodiments, this algorithm involves input from the user. A specific example of how a user can provide input for the measure of uncertainty is provided in FIGS. 3A-3B. FIG. 3A illustrates a an example embodiment of a computing device 9 wherein the computing device 9 is a smart phone 9 with the display 13, the smart phone 9 having a camera for image capture, with a line for the image capture 23 shown. FIG. 3B illustrates the display 13 of the smart phone of the computing device illustrating a query from the smart phone to determine from the user the measure of the certainty of the carbohydrate estimate. The smart phone can query the user, such as asking "How sure are you of the carbohydrate estimate?" The user can provide an answer from an array of choices, such as: A. Certain—looked it up on my phone or my phone provided an estimate based on a captured image, B. Pretty sure, making a reasonable estimate based on similar meals, or C. Unsure—guessing. The smart phone can have an image database against which to check carbohydrate levels for various foods, and can incorporate multiple images for one or more foods to provide an estimate. The smart phone can also ask follow-up questions such as the meal size, weight, or facts such as when previous meals were eaten and what the contents of such meals were. The smart phone can also provide and display suggested percentage ranges with each of A-C; for example A could be more than 75% sure, B could be 50-75 percent sure, and C could be less than 50% sure. If the uncertainty is below a certain level (such as under 75%, or 50% or under 25%, follow-up questions or alarms can be set to alert the user than not enough information has been provided for the device to provide recommendations. In the case where B was selected, in a specific embodiment that choice would activate the processor to access history of estimates of the user to determine previous accuracy; it can also determine how many times the user had eaten the same or a similar mean over previous time periods (such as every three or every four months), and compare the intervals to determine if the accuracy of estimates by determining if the user is getting better at estimates regarding the type of meal over time (if so the certainty will automatically be adjusted by the smart phone which can also automatically calculate factors such as standard deviation for each time period and if there are three or more increasing levels of accuracy for the last three periods, then the latest can be used if preferred and/or if pre-set to do such). Results of the algorithm as described herein can be provided on the display (displayed on the display).

Figure 4:
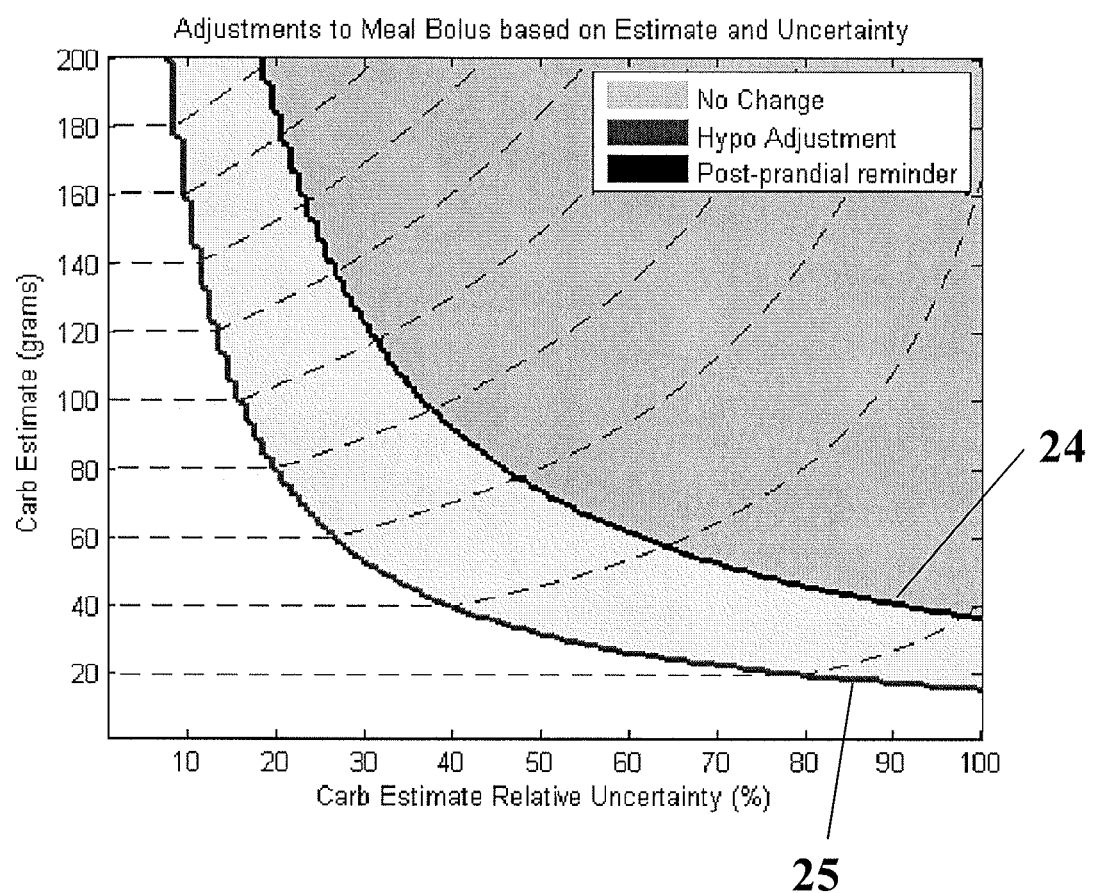
FIG. 4 illustrates an example of meal bolus advice using methods described herein for an individual with a carbohydrate ratio of 10 grams/IU and an insulin sensitivity factor of 30 milligrams per deciliter per international unit (mg/dL/IU)

FIG. 4 illustrates an example of meal bolus advice using methods described herein for an individual with a carbohydrate ratio of 10 grams/IU and an insulin sensitivity factor of 30 mg/dL/IU. The carbohydrate estimate is graphed against the carbohydrate estimate uncertainty as a percentage. In this example the uncertainty is given as a relative uncertainty. When the uncertainty is lower there is no change to the bolus advice. For meal estimates with moderate uncertainty only a hypoglycemia adjustment is made to slightly reduce the meal bolus. As the uncertainty increases a post-prandial reminder is set due to the high likelihood of needing a post-prandial correction bolus. Lines are shown to indicate a level of post-prandial reminder 24, and a line 25 for a hypoglycemia adjustment.

Figure 5:
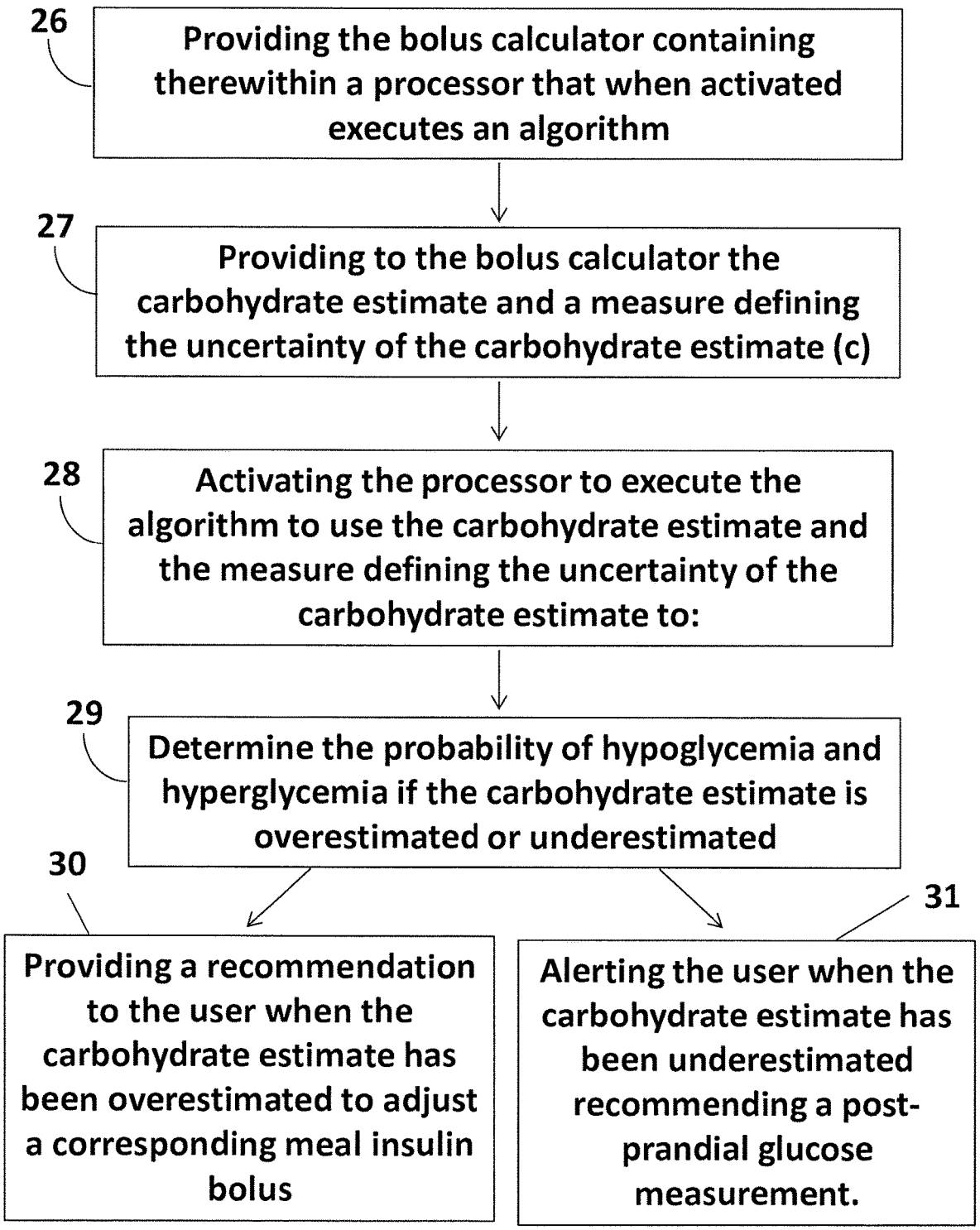
FIG. 5 illustrates a flowchart outlining a method of embodiments provided herein.

FIG. 5 illustrates a flowchart outlining a method of embodiments provided herein (26-31). In this specific embodiment steps can include one or more of: a method of using a bolus calculator to account for an uncertainty of a carbohydrate estimate to reduce a risk of hypoglycemia and a risk of hyperglycemia comprising: providing the bolus calculator containing therewithin a processor that when activated executes an algorithm; providing to the bolus calculator the carbohydrate estimate and a measure defining the uncertainty of the carbohydrate estimate (c); activating the processor to execute the algorithm to use the carbohydrate estimate and the measure defining the uncertainty of the carbohydrate estimate to: determine the risk(probability) of hypoglycemia and hyperglycemia if the carbohydrate estimate is overestimated or underestimated; providing a recommendation to the user when the carbohydrate estimate has been overestimated to adjust a corresponding meal insulin bolus, and alerting the user when the carbohydrate estimate has been underestimated recommending a post-prandial glucose measurement.

Uncertainty as described herein could come from one or more of: the filter, calibration routine, day of use for the sensor, sensor lot, and previous sensors worn by the individual, etc., or combinations thereof.

Embodiments herein detail calculations using an algorithm that improves the accuracy of the bolus calculator by accounting for uncertainty. The system becomes more accurate and faster with time as patterns emerge with the user estimates; for example the system could access part (such as one-third) of the estimates instead of all estimates once a baseline is understood as to the user accuracy of the user estimates so as to decrease time from estimate to display or results and/or advice.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A method of using a bolus calculator to account for an uncertainty of a carbohydrate estimate to reduce a risk of hypoglycemia comprising:
    providing the bolus calculator containing therewithin a processor that when activated executes an algorithm defining pre-set values for:
        a first threshold percentage defining a probability of hypoglycemia ($P_{hypo}$); and
        a hypoglycemia threshold ($T_{hypo}$);
    calculating, by the bolus calculator, a measure defining the uncertainty of the carbohydrate estimate (c) as a standard deviation ($\sigma_c$) based on (i) at least an assessment of an ability of a user to count carbohydrates from a test, (ii) a history of the user, or (iii) combination thereof;

providing to the bolus calculator the carbohydrate estimate;

activating the processor to execute the algorithm to use the pre-set values, the carbohydrate estimate and the measure defining the uncertainty of the carbohydrate estimate to:

determine the probability of hypoglycemia if the carbohydrate estimate has overestimated the carbohydrate content and therefore a standard meal insulin bolus has been overestimated and thus should be adjusted to reduce the risk of hypoglycemia:

providing a recommendation to the user when the carbohydrate estimate has been overestimated to adjust a corresponding meal insulin bolus; and administering the adjusted corresponding meal insulin bolus through a therapy delivery device operatively coupled to the bolus calculator to the user such that the administered adjusted corresponding meal insulin bolus affects a blood glucose value of the user to reduce the risk of hypoglycemia.

2. The method of claim 1 further comprising setting the threshold percentage defining the probability of hypoglycemia at about five percent.

3. The method of claim 1 further comprising setting the threshold percentage defining the probability of hypoglycemia at between about ten percent and twenty-five percent.

4. A method of using a bolus calculator to account for an uncertainty of a carbohydrate estimate to reduce a risk of hyperglycemia comprising:

providing the bolus calculator containing therewithin a processor that when activated executes an algorithm defining pre-set values for:
a threshold percentage defining a probability of hyperglycemia ($P_{hyper}$); and
a hyperglycemia threshold ($T_{hyper}$);

calculating, by the bolus calculator, a measure defining the uncertainty of the carbohydrate estimate (c) as a standard deviation ($\sigma_c$) based on at least (i) an assessment of an ability of a user to count carbohydrates from a test, (ii) a history of the user, (iii) or combination thereof;

providing to the bolus calculator the carbohydrate estimate;

activating the processor to execute the algorithm to use the pre-set values, the carbohydrate estimate and the measure defining the uncertainty of the carbohydrate estimate to:

determine the probability of hyperglycemia if the carbohydrate estimate has underestimated the carbohydrate content and therefore the standard meal insulin bolus has been underestimated and thus should be adjusted to reduce the risk of hyperglycemia;

alerting the user when the carbohydrate estimate has been underestimated recommending a post-prandial glucose measurement; and administering the adjusted corresponding meal insulin bolus through a therapy delivery device operatively coupled to the bolus calculator to the user such that the administered adjusted corresponding meal insulin bolus affects a blood glucose value of the user to reduce the risk of hyperglycemia.

5. The method of claim 4 further comprising setting the threshold percentage defining the probability of hyperglycemia at about seventy-five percent.

6. The method of claim 4 further comprising setting the threshold percentage defining the probability of hyperglycemia between about seventy percent to about eighty percent.

7. A bolus calculator to account for an uncertainty of a carbohydrate estimate to reduce a risk of hypoglycemia comprising:

a processor that when activated is configured to execute an algorithm defining pre-set values for:
a first threshold percentage defining a probability of hypoglycemia ($P_{hypo}$); and
a hypoglycemia threshold ($T_{hypo}$);

the processor is configured, upon receipt by the bolus calculator of the carbohydrate estimate, to:

calculate a measure defining the uncertainty of the carbohydrate estimate (c) as a standard deviation ($\sigma_c$) based on at least an assessment of an ability of a user to count carbohydrates from a test, a history of the user, or combination thereof;

determine the probability of hypoglycemia if the carbohydrate estimate has overestimated the carbohydrate content and therefore a standard meal insulin bolus has been overestimated and thus should be adjusted to reduce the risk of hypoglycemia in which the processor:

calculate the standard meal insulin bolus ($I_{meal}$) utilizing the carbohydrate estimate and a carbohydrate ratio of the user;

calculate, using the carbohydrate estimate, the standard deviation, and a parameter on a normal cumulative distribution, a carbohydrate level ($C_{Phypo}$) representative of a carbohydrate estimate at a percentage defined by $P_{hypo}$ as the first threshold percentage defining the probability of hypoglycemia;

calculate a hypoglycemia-averse insulin bolus ($I_{hypo(x)}$ %) using an insulin sensitivity factor of the user, the hypoglycemia threshold and the calculated carbohydrate level;

compare the standard meal insulin bolus with the hypoglycemia-averse insulin bolus;

select the minimum of the standard meal insulin bolus and the hypoglycemia-averse insulin bolus thereby accounting for the risk of hypoglycemia;

administer the selected minimum bolus through a therapy delivery device operatively coupled to the bolus calculator to the user such that the administered selected minimum bolus affects a blood glucose value of the user to reduce the risk of hypoglycemia.

8. The bolus calculator of claim 7 further comprising a physically separate memory coupled to the bolus calculator such that the standard deviation is derived in part from the medical history of the user stored in the memory.

9. The bolus calculator of claim 7 wherein the bolus calculator contains a memory therewithin such that the standard deviation is derived in part from previous determinations of the user as to an ability to estimate carbohydrates which have been previously stored in the memory.

10. The bolus calculator of claim 7 wherein the bolus calculator is coupled to a memory such that the standard deviation is derived in part from previous tests provided to the user testing estimating carbohydrates which have been previously stored in the memory.

11. The bolus calculator of claim 7 wherein the bolus calculator is configured to query the user, to ask for the carbohydrate estimate.

12. The bolus calculator of claim 7 wherein the bolus calculator is configured to query the user, to ask of the certainty of the carbohydrate estimate provided by the user, and provide the user with options detailing the uncertainty that can be selected via buttons on a display of the bolus calculator.

13. The bolus calculator of claim 7 wherein the processor is configured to provide, visually via a display of the bolus calculator, an alert to the user which instructs the user to take the post-prandial glucose measurement.

14. A bolus calculator to account for an uncertainty of a carbohydrate estimate to reduce and a risk of hyperglycemia comprising:
   a processor that when activated is configured to execute an algorithm defining pre-set values for:
      a threshold percentage defining a probability of hyperglycemia ($P_{hyper}$); and
      a hyperglycemia threshold ($T_{hyper}$);
   the processor is configured, upon receipt by the bolus calculator of the carbohydrate estimate, to:
      calculate a measure defining the uncertainty of the carbohydrate estimate (c) as a standard deviation ($\sigma_c$) based on at least an assessment of an ability of a user to count carbohydrates from a test, a history of the user, or combination thereof;
      determine the probability of hyperglycemia if the carbohydrate estimate has underestimated the carbohydrate content and therefore a standard meal insulin bolus has been underestimated and thus should be adjusted to reduce the risk of hyperglycemia in which the processor:
      calculate, using the carbohydrate estimate, the standard deviation, and a parameter on a normal cumulative distribution, a carbohydrate level ($C_{Phyper}$) representative of a carbohydrate estimate at a percentage defined by $P_{hyper}$ as the threshold percentage defining the probability of hyperglycemia;
      calculate, using the calculated carbohydrate level, a user insulin sensitivity factor, and a target glucose level, a value representing a post-prandial glucose estimate;
      compare the value to the hyperglycemia threshold;
      provide an alert to the user instructing the user to take a post-prandial glucose measurement when the value is greater than the hyperglycemia threshold, thereby accounting for the risk of hyperglycemia, and
      administer the adjusted corresponding meal insulin bolus through a therapy delivery device operatively coupled to the bolus calculator to the user such that the administered adjusted corresponding meal insulin bolus affects a blood glucose value of the user to reduce the risk of hyperglycemia.

15. The bolus calculator of claim 14 further comprising a physically separate memory coupled to the bolus calculator such that the standard deviation is derived in part from the medical history of the user stored in the memory.

16. The bolus calculator of claim 14 wherein the bolus calculator contains a memory therewithin such that the standard deviation is derived in part from previous determinations of the user as to an ability to estimate carbohydrates which have been previously stored in the memory.

17. The bolus calculator of claim 14 wherein the bolus calculator is coupled to a memory such that the standard deviation is derived in part from previous tests provided to the user testing estimating carbohydrates which have been previously stored in the memory.

18. The bolus calculator of claim 14 wherein the bolus calculator is configured to query the user, to ask for the carbohydrate estimate.

19. The bolus calculator of claim 14 wherein the bolus calculator is configured to query the user, to ask of the certainty of the carbohydrate estimate provided by the user, and provide the user with options detailing the uncertainty that can be selected via buttons on a display of the bolus calculator.

20. The bolus calculator of claim 14 wherein the processor is configured to provide, visually via the display, the alert to the user which instructs the user to take the post-prandial glucose measurement.

* * * * *